United States Patent [19]

Smethers et al.

[11] Patent Number: 5,716,583
[45] Date of Patent: Feb. 10, 1998

[54] LUMINOMETER WITH REDUCED SAMPLE CROSSTALK

[76] Inventors: Rick T. Smethers, 1233 Valdez St., Freemont, Calif. 94539; Brian D. Warner, 1034 Alhambra Ave., Martinez, Calif. 94553; Victor P. Burolla, 1322 Shawnee Rd., Livermore, Calif. 94550

[21] Appl. No.: 411,445

[22] Filed: Mar. 28, 1995

Related U.S. Application Data

[62] Division of Ser. No. 878,829, May 5, 1992, Pat. No. 5,401,465.

[51] Int. Cl.⁶ .................................................. G01N 21/29
[52] U.S. Cl. .................. 422/82.05; 422/52; 422/82.08; 422/102; 436/164; 356/338; 356/213
[58] Field of Search .................................. 422/52, 82.08, 422/82.05, 102; 436/164; 356/338, 213

[56] References Cited

U.S. PATENT DOCUMENTS

| | | |
|---|---|---|
| 3,700,338 | 10/1972 | Trundle . |
| 3,759,374 | 9/1973 | Helger et al. . |
| 3,997,404 | 12/1976 | Waters . |
| 4,115,010 | 9/1978 | McAleer et al. . |
| 4,213,703 | 7/1980 | Haunold et al. . |
| 4,350,495 | 9/1982 | Broutman et al. . |
| 4,586,818 | 5/1986 | Lohr . |
| 4,745,077 | 5/1988 | Holian et al. . |
| 4,772,453 | 9/1988 | Lisenbee . |
| 5,401,465 | 3/1995 | Smethers et al. . |

FOREIGN PATENT DOCUMENTS

| | | |
|---|---|---|
| 4123817 | 1/1993 | Germany . |

*Primary Examiner*—Paula K. Hutzell
*Assistant Examiner*—Heather A. Bakalyar
*Attorney, Agent, or Firm*—Judy M. Mohr; Kenneth M. Goldman; Robert P. Blackburn

[57] ABSTRACT

A luminometer is described comprising a tray for receiving an array of sample wells, a photodetector assembly, and means for relatively moving the tray and photodetector assembly in one direction to align the sample wells received by the tray in a predetermined sequence with the photodetector assembly. The photodetector assembly of the luminometer includes a stage, a photodetection head having a detection aperture permitting passage of light therethrough, a means for mounting the photodetection head to the stage that permits movement of the head in a direction substantially normal to the direction of relative tray and photodetector assembly movement, and a means for biasing the photodetection head toward a selected sample well so that the detection aperture is substantially isolated from light emitted from adjacent wells. Internal and external photodetector calibration systems and a sample heater are also contemplated.

2 Claims, 8 Drawing Sheets

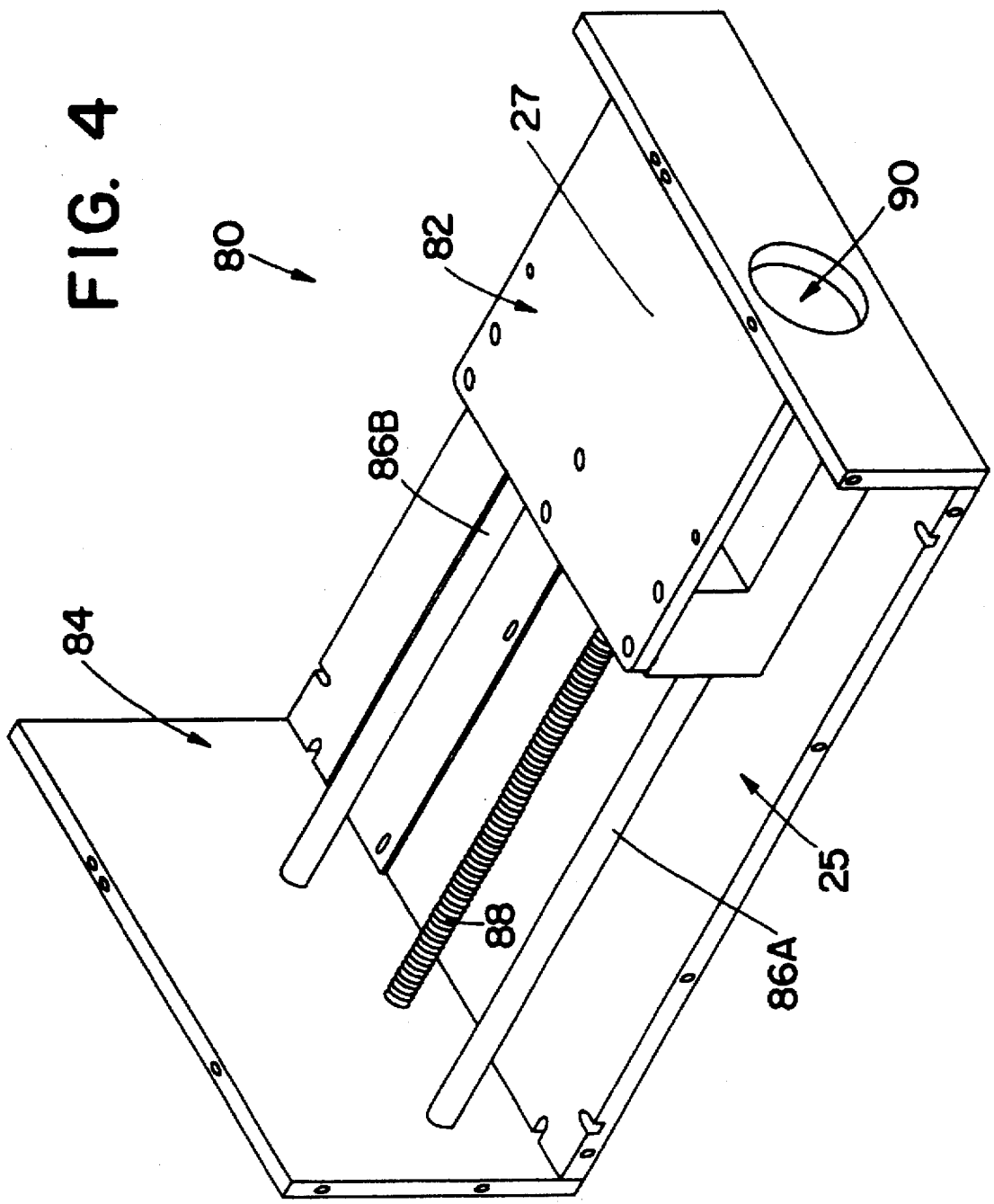

LUMINOMETER WITH REDUCED SAMPLE CROSSTALK

This is a division of application Ser. No. 07/878,829, filed 5 May 1992, now U.S. Pat. No. 5,401,465.

TECHNICAL FIELD

The present invention relates to detection systems for measuring the luminescence of biological samples contained in a plurality of sample wells.

CITED REFERENCES

1. U.S. Pat. No. 4,772,453 to Lisenbee;
2. U.S. Pat. No. 4,563,331 to Losee et al.;
3. U.S. Pat. No. 4,366,118 to Bunce et al.;
4. U.S. Pat. No. 4,099,920 to Heiss;
5. European Patent Publication 0025350.

BACKGROUND OF THE INVENTION

The phenomenon of luminescence, either chemiluminescence (CL) or bioluminescence (BL), is increasingly being exploited in quantitative determinations of a variety of analytes. For instance, the bioluminescent signatures of planktonic organisms have been studied in efforts to determine the species responsible for bioluminescence [U.S. Pat. No. 4,563,331].

Recently, methods for quantitating an analyte in an immunoassay protocol have been proposed which utilize luminescence detection. Such luminescence immunoassays (LIA) offer the potential of combining the reaction specificity of immunospecific antibodies with the high sensitivity available through light detection. The specificity and sensitivity of LIA reagents is generally comparable to those employing traditional radiolabelling. However, the nontoxic nature of LIA reagents and the longer shelf lives of LIA reagents relative to radioactive reagents makes LIA a generally preferred analytical method for many applications.

One exemplary bioluminescent reaction involves firefly luciferase, which mediates the conversion of luciferin to oxidation products and light. Assays of ATP using the firefly reaction have been reported to be linear over six orders of magnitude with a detection limit of $10^{-4}$ picomol of ATP [U.S. Pat. No. 4,772,453].

Not surprisingly, much interest has evolved in developing improved instruments for measuring luminescence from biological samples. Since many samples are frequently screened concurrently, e.g., for immunoreaction of a bioluminescent antibody with a target analyte, low light levels from external light sources or adjacent samples can be problematic. The instruments designed to measure the low light levels associated with luminescence are frequently referred to herein as luminometers.

Some previously proposed luminometers include those described in U.S. Pat. No. 4,772,453; U.S. Pat. No. 4,366,118; and EP 0025350. U.S. Pat. No. 4,772,453 describes a luminometer having a fixed photodetector positioned above a platform carrying a plurality of sample cells. Each cell is positioned in turn under an aperture through which light from the sample is directed to the photodetector. U.S. Pat. No. 4,366,118 describes a luminometer in which light emitted from a linear array of samples is detected laterally instead of above the sample. Finally, EP 0025350 describes a luminometer in which light emitted through the bottom of a sample well is detected by a movable photodetector array positioned underneath the wells.

Further refinements of luminometers have been proposed in which a liquid injection system for initiating the luminescence reaction just prior to detection is employed [EP 0025350]. Also, a temperature control mechanism has been proposed for use in a luminometer [U.S. Pat. No. 4,099,920]. Control of the temperature of luminescent samples may be important, for example, when it is desired to incubate the samples at an elevated temperature.

However, none of the above devices effectively avoids detection of light emitted by samples in adjacent sample wells, i.e., those not intended to be monitored when a measurement is made on a given sample. Hence, the previous devices can fail to accurately determine the light level emitted by a weakly emitting sample, particularly when it is adjacent one or more strongly emitting sample(s). This phenomenon of light measurement interference by adjacent samples is frequently referred to herein as "crosstalk".

SUMMARY OF THE INVENTION

The present invention includes, in one aspect, an improved luminescence measurement apparatus (luminometer). The luminometer has a platform for carrying an array of sample wells, where each well has a structure defining a window through which light can be emitted. Also included in the luminometer are a photodetector assembly, and a structure for relatively moving the platform and photodetector assembly in at least one direction, to align the sample well windows in a predetermined sequence with the photodetector assembly. In the improvement of the invention, the photodetector assembly includes: (i) a stage positionable adjacent each of the sample wells; (ii) a photodetection head having a detection aperture permitting passage of light therethrough; (iii) structure for mounting the photodetection head on the stage for movement of the head toward and away from a sample-reading position at which the detection aperture is substantially isolated from light emitted from adjacent sample wells, when such wells are received in said tray and the detection aperture is aligned with the window of the selected sample well; and (iv) structure biasing the photodetection head toward its sample-reading position.

In one embodiment, the platform for carrying the sample wells and the photodetector assembly are relatively movable in an x-y plane, and the structure mounting the photodetection head to the stage permits movement of the head in a direction substantially normal to the x-y plane of the wells, i.e., in the z direction.

Also contemplated in the luminometer is a photodetector internal-calibration system. The system includes a hermetically sealed chamber and a means for controlling the temperature of the chamber. Contained within the chamber is a light source, a photosensor for detecting light emitted from the light source, and means for directing the light from the light source to the photodetection head of the photodetector assembly when the assembly is positioned at an internal calibration station. The system includes a feedback circuit for maintaining the light intensity of the light source substantially constant.

Further contemplated is a photodetector external-calibration system for use with a luminometer of the present invention. The calibration system, which is receivable by a luminometer platform, includes a light source, a plurality of light wells, each defining a window through which light can be emitted, and a plurality of channels, each permitting passage of light from the light source to one of the light wells. Also included is an aperture associated with each channel for producing a predefined ratio of light intensities in the light wells. That is, each of the apertures differ in size in order to produce the desired ratio of light intensities.

A further embodiment of a luminometer constructed according to the present invention includes a tray-heating plate and structure for spacing the sample tray from the heater in heating relationship thereto. The samples in the tray are thereby heated substantially uniformly, by radiant heat.

A further preferred aspect of the invention employs an adhesive film covering the sample wells. The film serves to reduce the coefficient of friction between the photodetector head and the sample wells when the photodetector assembly is moved relative to the tray. A particularly preferred adhesive film is a transparent polymer film having a thickness of between about 0.001 and 0.01 inches.

Also contemplated is a method of detecting light emitted from one of a plurality of luminescent samples in a luminometer. The method includes positioning a photodetector head adjacent a sample well containing a luminescent sample to be measured, while biasing the photodetection head against the sample well, thus permitting the head to detect light emitted by the sample being monitored, but to substantially isolate the head from light emitted by adjacent samples. In a preferred method an adhesive film is placed over the sample wells and the photodetection head is biased against the film and a sample well.

These and other objects and features of the invention will become more fully apparent when the following detailed description of the invention is read in conjunction with the accompanying drawings.

BRIEF DESCRIPTION OF THE DRAWINGS

FIG. 4 shows a perspective view of a platform carriage unit constructed according to the present invention.

DETAILED DESCRIPTION OF THE INVENTION

I. Luminometer

Figure 1:
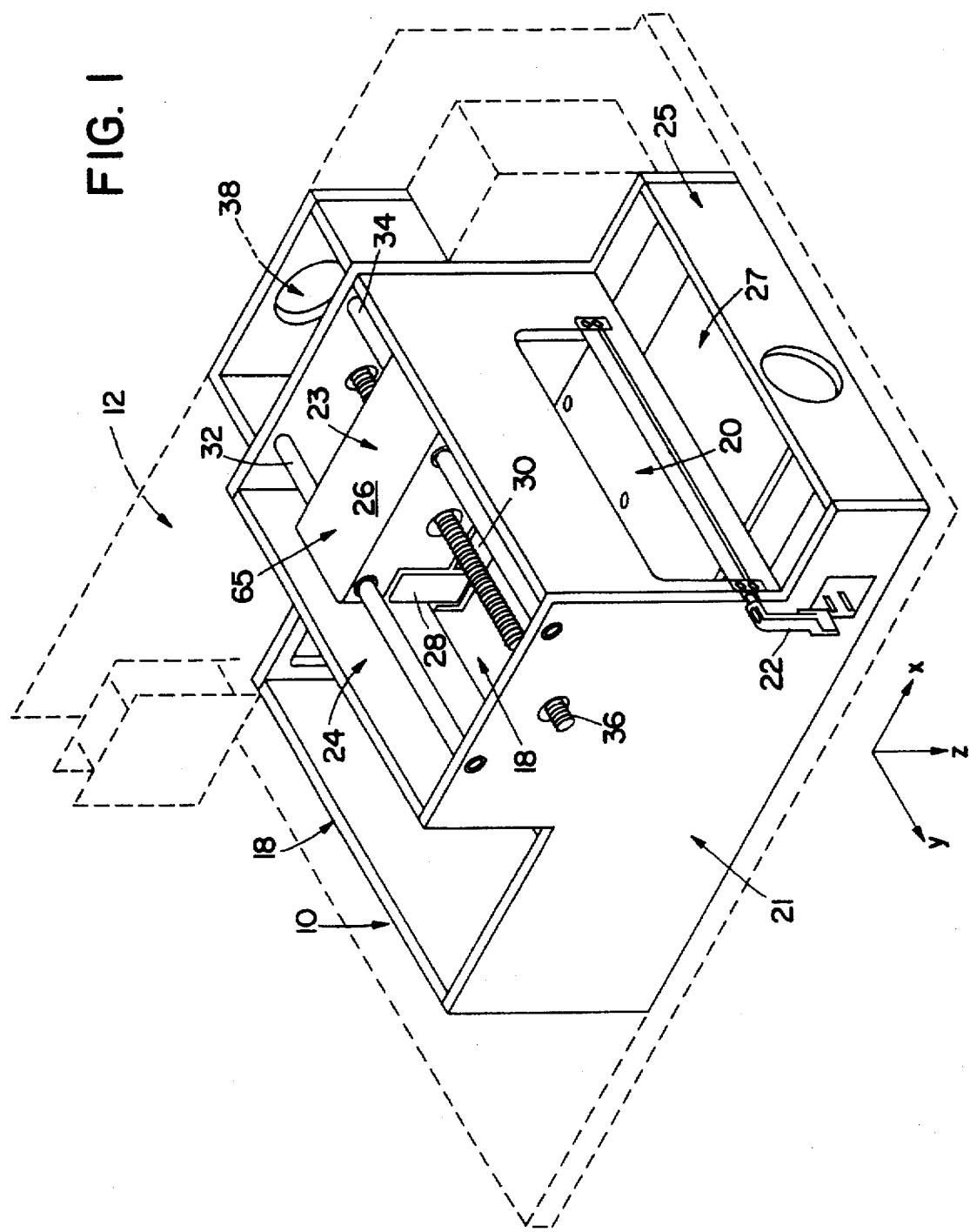
FIG. 1 is a perspective view of portions of a luminometer constructed according to the present invention.

Depicted in FIG. 1 is a preferred embodiment of a luminometer 10 constructed according to the principles of the present invention. The luminometer includes a lightproof housing 12, lower and side portions of which are shown in dotted lines in FIG. 1. The housing defines an internal test chamber 18 in which luminescence measurements are performed. Luminometer 10 also includes a control panel (not shown) at which a user interface is provided for controlling the parameters of a given luminescence determination.

Also shown in the figure are a photodetector carriage unit 21 on which is mounted a photodetector assembly 23, described below with respect to FIGS. 2 and 3, respectively, and a platform carriage unit 25 described below in FIG. 4. As seen in the figure, the platform carriage unit is positioned below photodetector carriage assembly. A platform 27 in unit 25 defines an x-y plane which is adapted to receive a tray loaded with a planar array of sample wells to be analyzed in the luminometer, in a manner to be described. With respect to the x-y-z axes shown in FIG. 1, the platform defines an x-y plane in which the planar array of sample can be moved relative to the photodetector in the luminometer. The platform is designed to receive a sample-holding tray, as described below.

Figure 2:
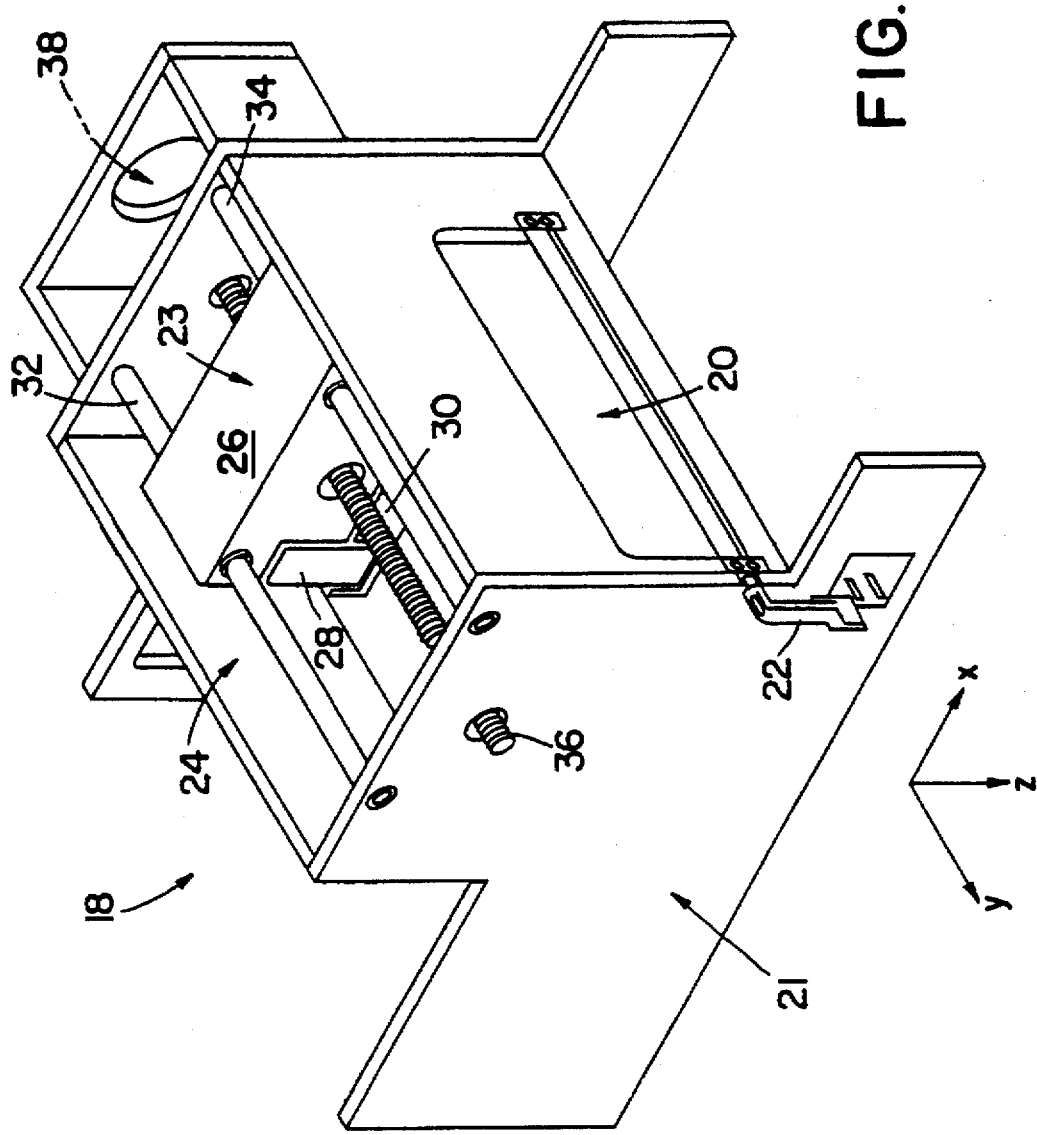
FIG. 2 shows a perspective view of a photodetector carriage unit constructed according to the present invention.

With reference to FIGS. 1 and 2, unit 23 is provided with an opening 20 through which platform 27 can pass, when a tray is extended to a load/unload position outside of the luminometer housing, along axis x in the figure. A handle 22 controls operation of a door (not shown) for sealing opening 20 against light entry into the luminometer chamber.

Figure 3A:
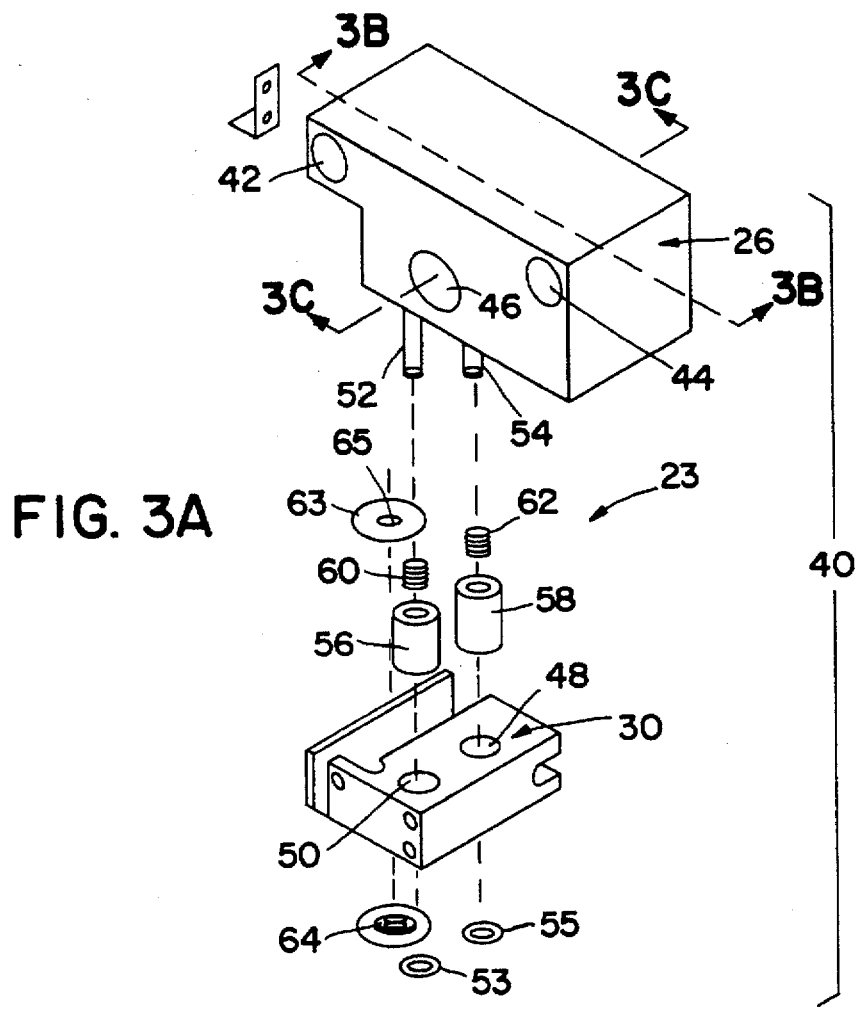
FIG. 3A shows an exploded view of a photodetector assembly constructed according to the present invention.

Also forming part of the carriage unit is a photodetector assembly 23 comprising a block or stage 26, a photodetector 28, and photodetector support 30, as will be described below with respect to FIGS. 3A and 3B. As shown in the FIG. 2, block 26 is supported within unit 23 by two parallel guide shafts 32 and 34 which extend between two opposing walls of the unit. Providing a further means of support for block 26 is lead screw 36, which is parallel to shafts 32 and 34 and extends through a wall of chamber 18 in centered alignment with a drive port 38. Drive port 38 receives an electric motor, such as a conventional stepper motor, (not shown) that can turn screw 36 a selected rotational angle to advance the block a desired forward or backward along axis y in FIG. 1. More specifically, the block is movable to a plurality of sample-read positions at which a photodetector unit carried on the block is positioned to read selected-position sample wells carried on platform 27 in the luminometer, as will be seen below. Turning to FIG. 3A, an exploded view of portions of a photodetector assembly in carriage unit 23 is shown. The assembly includes a block 26 with guide bores 42, 44 through which pass shafts 32 and 34, respectively. Also, a bore 46 is provided in block 26 through which passes lead screw 36.

The block has a pair of downwardly extending posts 52, 54 on which a support 30 in the assembly is movably mounted. Support 30 provides bores 48 and 50 through which mounting posts 52 and 54, which are countersunk in block 26, can pass. Snap rings 53 and 55 which attach to posts 52 and 54 are provided under photodetector support 30 and secure the support to the mounting posts. To promote low frictional movement of photodetector support 30 along posts 52 and 54, bearings 56 and 58 are provided within bores 50 and 48. Block 26 and photodetector support 30 can be constructed from any solid material, such as aluminum or a high density polymer.

Springs 60 and 62 are provided between block 26 and photodetector support 30 and are secured in place with post 52 and 54 which pass through the centers of springs 60 and 62. Preferably, springs 60 and 62 ride on top of bearings 56 and 58 to ensure vertical displacement of the springs when they are compressed. Springs 60 and 62 thereby provide means for biasing photodetector support 30 away from block 26.

Figure 3B:
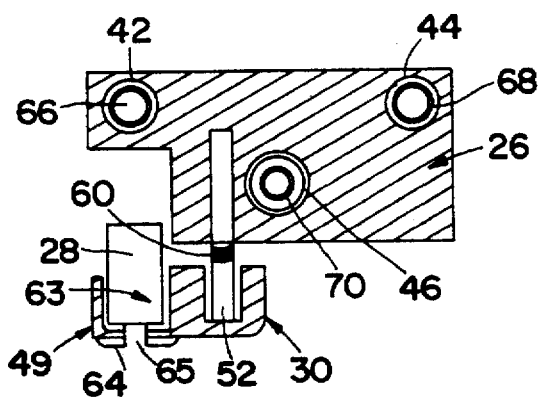
FIGS. 3B and 3C show sectional views of the same device taken along lines 3B—3B and 3C—3C, respectively, in FIG. 3A.
Figure 3C:
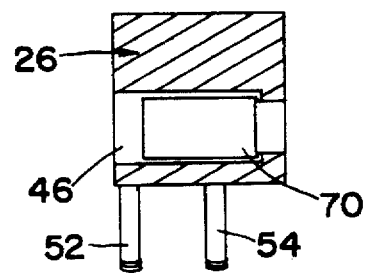

FIG. 3B shows a sectional view of block 26 and photodetector support 30 and FIG. 3C shows a second sectional view of block 26. As seen, bearings 66 and 68 are positioned within bores 42 and 44 of block 26. Also, nut 70 having a threaded interior, is secured within bore 46 and permits passage of lead screw 36 therethrough.

Also shown in FIG. 3B is photodetector unit 28 which is carried in the U-shaped cavity 63 provided in support 30. Unit 28 is preferably a conventional photomultiplier tube (PMT), such as unit HC-120-03 available from Hamamatsu (Japan). The unit receives light from sample wells through an aperture 65 formed in a plastic disc 64 carried at the lower side of support 30. The disc is formed of an opaque, preferably low-friction polymer such as DELRIN, a polyacetal, TEFLON or polyethylene. The disc is secured in place by threaded attachment to the bottom of the support, as seen below in FIG. 5A.

Support 30, including disc 64, and the PMT carried in the support, are also referred to herein, collectively, as a photodetector head having a detection aperture (defined by disc 64).

It will be appreciated from FIG. 3B that posts 52, 54 in stage 26, and bearings 56, 58 through the posts are received form means mounting the support, i.e., the photodetector head, along the z axis in FIG. 1, i.e., in a direction substantially normal to the x-y plane defined by platform 27. Functionally, this mounting means allows movement of the photodetector head toward and away from a sample-reading position at which the detection aperture is substantially isolated from light emitted from adjacent wells, as described below with respect to FIG. 5A. The photodetector head is biased toward its sample-reading position (in a downward direction in the figure) by the biasing means formed by springs 60,62.

Block or stage 26, the photodetector head, the means mounting the head for movement toward and away from its sample reading position, and the biasing means biasing the head toward its sample-reading position collectively form photodetector assembly 23.

With reference to FIG. 4, the platform carriage unit in the luminometer includes platform 27 which is moveable slidably along shafts 86A and 86B which pass through a block of platform 27, in much the same fashion as the photodetector carriage 40 described above. Lead screw 88 extends between platform 82 and a wall of carriage 80. Lead screw 88 is centrally aligned with drive port 90 in which an electric motor, such as a conventional stepper motor, (not shown) is positioned for attachment to lead screw 88. Actuation of the motor serves to advance the platform a desired distance in the direction of the x axis in FIG. 1. More specifically, the platform is movable by the motor from an extended load/unload position, in which the platform is accessible for loading and unloading outside the luminometer housing, and to a plurality of sample-read positions in which one row of sample wells in a sample array on the platform is aligned for reading by the photodetector unit.

A control unit (not shown) activates the motor as required to position a sample tray at a predefined read or load position.

It will be appreciated that the present invention is not limited to use of planar x-y arrays of sample wells. Linear arrays of sample wells obviously can also be employed, in which a tray for the wells would likely contain only a row of wells. Alternatively, a circular array, e.g., a carousel, of sample wells can also be used with the present invention. Detection of light emitted from the wells can be performed with an instant photodetector assembly positioned above, below, or adjacent a side wall of a well under test. It should be noted that the direction of movement of a carousel tray containing a plurality of sample wells is tangential to the periphery of the carousel and would be substantially normal to the direction of movement of the photodetection head.

Figure 5A:
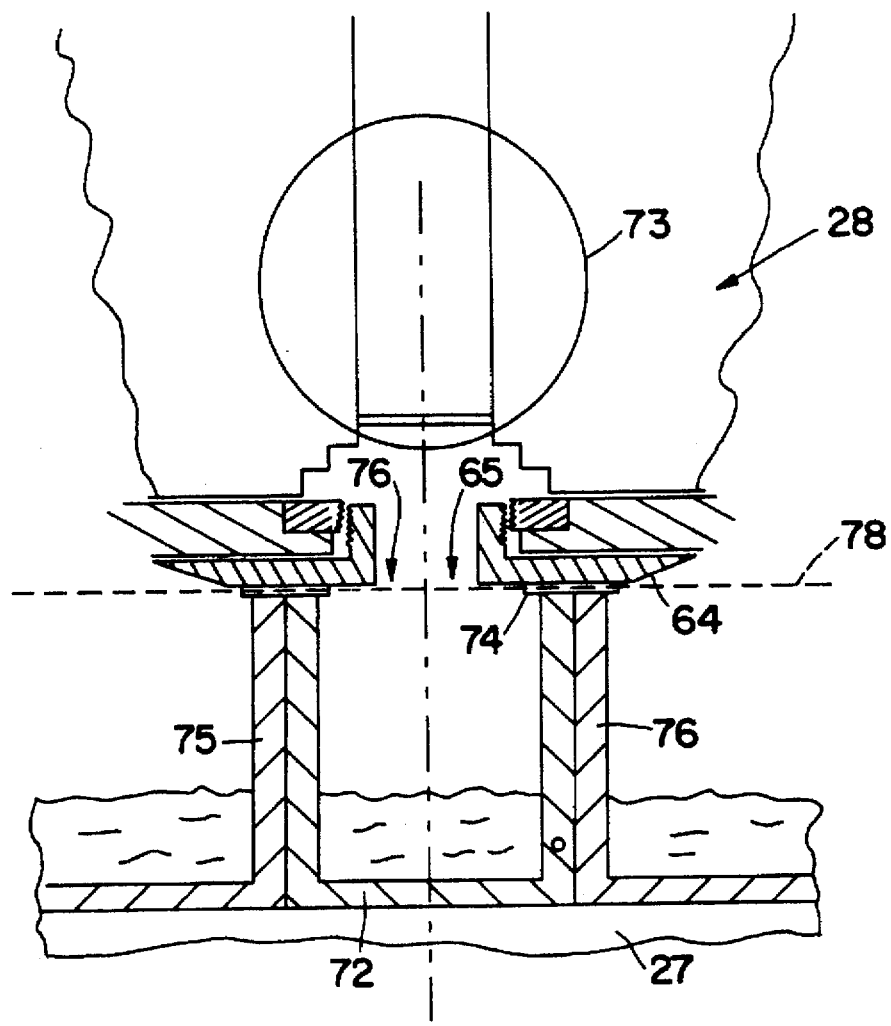
FIG. 5A illustrates a preferred aspect of the invention in which detection of light emission from a sample well covered by an adhesive film is depicted with a photodetector head and sample tray shown in cross-section.

FIG. 5A illustrates how the luminometer described above functions to prevent crosstalk, i.e., light contamination between a selected cell being read by the photodetector head and an adjacent well. The figure shows in cross-section a sample well 72 which is representative of one of a plurality of sample wells in a planar array of wells in a tray carried on platform 27. The wells are typically formed from opaque polystyrene. One suitable type of sample well is available in sample well strips from Dynatech. Well 72, which is representative, has an upper edge 74 which defines a circular window or aperture 76 in the well. In a preferred embodiment, the upper edges of the wells are covered by a clear film 78 having an adhesive backing on its lower side (the side in contact with the sample windows), effectively sealing each sample well against loss of moisture. The film functions both as a vapor barrier and can also prevent contamination of samples by dust, etc. The film preferably is between about 0.001 and 0.01 inches, i.e., between about 1 and 10 mils. One preferred polymeric film is MYLAR, preferably about 2–3 mils thick. The MYLAR can also be coated on its sample-facing side with a chemically resistant, e.g., water insoluble, adhesive to promote adherence of the film to the sample wells. The film is preferably resistant to elevated temperatures, e.g., up to about 65° C.

Significantly, when a film is used with the embodiment of the invention shown in FIG. 5A, it also serves to reduce friction between the photodetector assembly and the upper edges of the wells, as the two are moved relatively as the sample wells are read.

Also shown in FIG. 5A is a lower portion of the photodetector head, with such in its sample-reading position. As can be appreciated from the above description of the photodetector head, i.e., disc 64, is pressed against the upper edge of the aligned sample well by the biasing of springs 60, 62 in the assembly. With reference again to FIG. 5A, this biasing serves to isolated the PMT (shown at 73) from light emitted from adjacent wells, such as adjacent wells 75, 76 shown in the figure, essentially by closing the gap between the upper edges of adjacent sample wells and the aperture of the PMT. Specifically, the only light path available between adjacent wells and the PMT aperture is the thin film 78 separating the upper edges of the sample and disc 64.

If desired to limit light contamination between adjacent samples still further, film 78 can be modified to contain a light absorbing material with the film, either as a separate film or impregnated within the polymer. An absorbent material would slightly attenuate light traveling directly through the film to the photodetector, but would, by virtue of the relatively long light path between adjacent wells, substantially eliminate light travel between wells via the film.

Figure 5B:
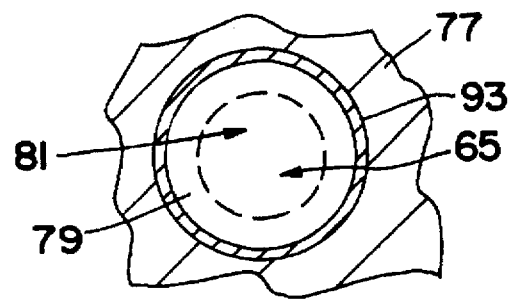
FIG. 5B shows an exemplary alignment of a detection aperture with a sample well window.

Alternatively, the film may have an opaque coating which covers an outer portion of the window defined in each sample well. FIG. 5B illustrates a film 77 having an opaque coating 79 which forms an opaque region adjacent the outer edge of a sample well, defining therewith structure defining a window 81 in the center region of the well. Similarly, when an adhesive is used with the film it is preferred that an adhesive is selected which minimizes light scattering.

The invention also contemplates a detection system for measuring luminescence in each of a plurality of samples. The system includes a planar array of sample wells, each having an upper edge structure defining a window through which light can be received, and a photodetector assembly having (i) a stage, (ii), a photodetector head having a means defining an aperture, (iii) means for mounting the photodetection head on the stage for movement of the head toward and away from a sample-reading position at which the detection aperture is substantially isolated from light emitted from adjacent sample wells, when such wells are received in said tray and the detection aperture is aligned with the window of the selected sample well, and (iv) means for biasing the photodetection head toward its sample-reading position, and means for relatively moving the photodetector assembly and sample array in a plane which is substantially normal to the direction of movement of the photodetector head toward and away from its sample-read position, to successively align each well in the array with the photodetector assembly, with such relative movement being accommodated by movement of the photodetector head toward and away from its sample-read position.

II. Method of Luminometer Reading

In another aspect, the invention includes a method of detecting light emitted from one of a plurality of luminescent samples. The method includes first positioning a photodetection head adjacent a sample well containing a luminescent sample. This is done, in the luminometer described above, by moving the photodetection head and platform relatively to align the photodetector aperture sequentially with the window in each sample well. In a typical luminometer operation, a tray filled with a planar array of sample wells is placed on the luminometer platform, with such in its load/unload position, and the wells are positioned for successive reading by the photodetection head, as described below.

As discussed above, the method permits the head to detect light emitted by the sample under test and to substantially isolate the head from light emitted by the remaining samples. This is done in the embodiment illustrated above, by biasing the photodetection head against the sample well and an intervening transparent film.

At each sample well, the detection aperture of the photodetection head is aligned (in registry) with a window defined in the sample well. The periphery of the aperture corresponds approximately to the "clear" central portion of the film above in FIG. 5B. As seen, the periphery of aperture is positioned within the periphery of a window of the sample well. The periphery of the window may be defined by the edge of the sample cell, or in the embodiment shown in FIG. 5B, by the clear portion of the film.

After a light measurement is taken from one sample well, the photodetection head is moved successively to read the wells in that row. The platform is then advanced to align the photodetection head with the next row of wells, and the sample wells in this row are then read by movement of the photodetection head, as above. As can be appreciated in FIG. 5A, the photodetector head "floats" ("rides") over the edges of the sample wells as the sample tray is moved relative to head 28. Accordingly, the head is so biased against a sample well when light from the well is being detected that the head (or a support for the head) contacts the sample well under test. It is understood that a photodetector head is said to be biased against a sample well whenever a film actually is interposed between the head and sample well.

III. Heating System.

Figure 6:
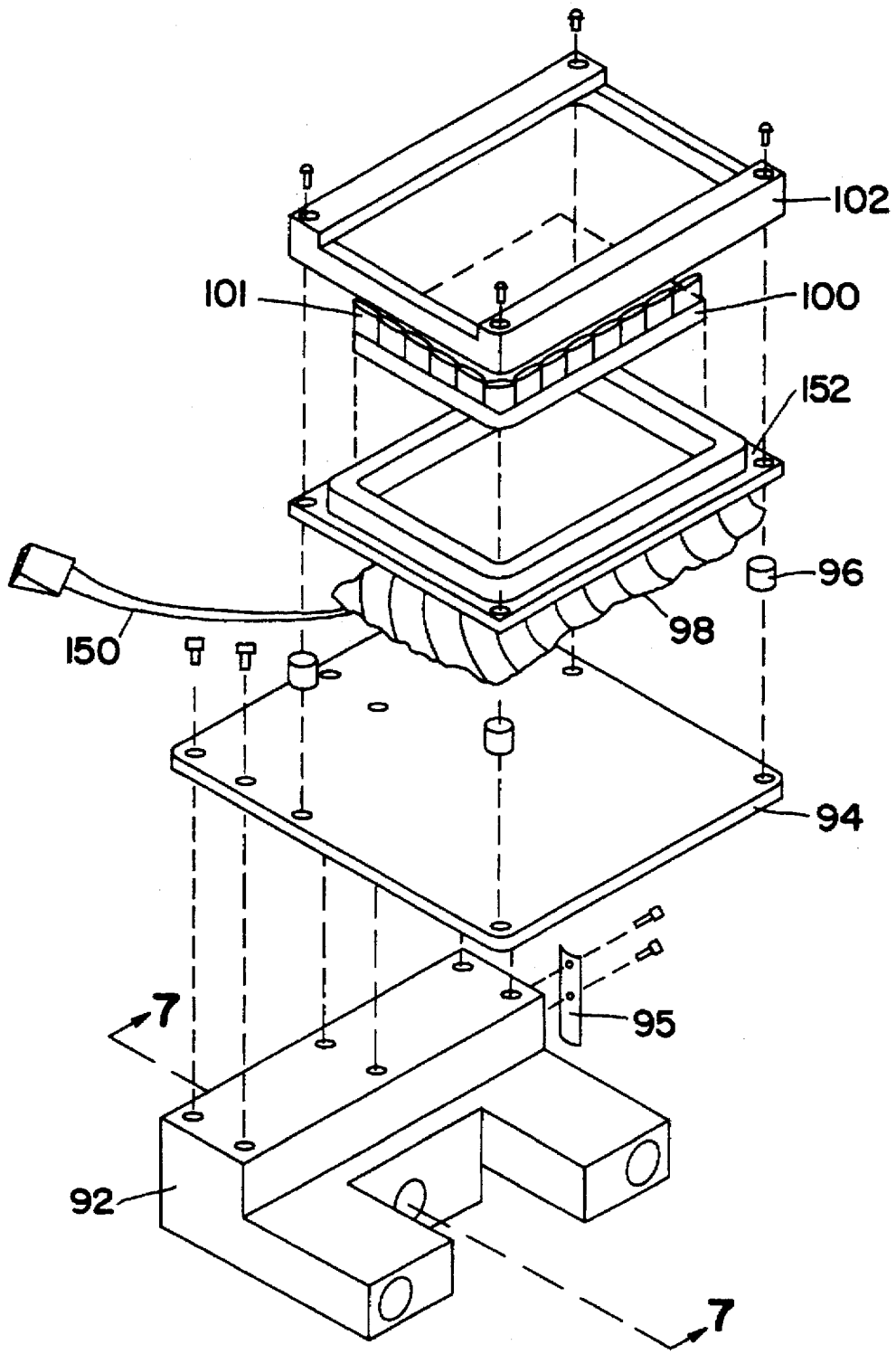
FIG. 6 shows an exploded view of a sample heater assembly constructed according to the present invention.

Shown in FIG. 6 is an exploded view of sample platform 27, as well as a means for radiantly heating a set of samples. As seen in the figure, the platform includes a base 92 and a plate 94. Also shown is a heating coil 98 formed of a foil heater encapsulated in silicone and having an adhesive backing. Current is supplied to the coils in the heater through electrical connections 150. The silicon, which is interspaced between the tray from the foil heater, provides means for spacing the tray from the heater plate, and allows more even heat distribution from the heater to the tray.

Tray support 152 is positioned in a spaced-apart relationship with plate 94 through the use of four spacers 96. Such spaced-apart relationship helps to direct heat evenly to the tray support. Also shown in the figure is an exemplary tray 100 for receiving a plurality of sample wells, such as well 101. The sample wells may have a variety of shapes and sizes, with the limitation that the wells do not allow light contamination from their side walls to adjacent wells. Tray 100 rests on tray support 98, and is confined from lateral movement by frame 102.

Figure 7:
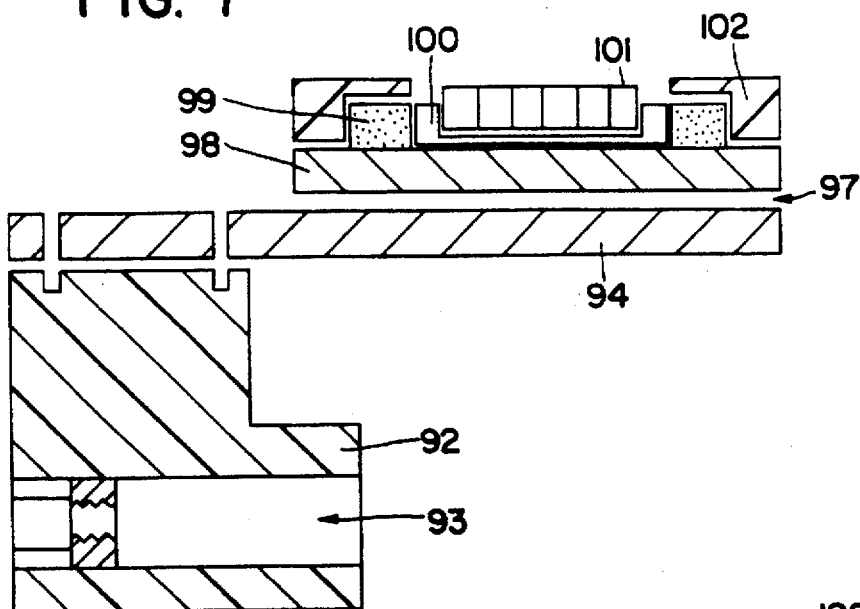
FIG. 7 shows a sectional view of the heater assembly shown in FIG. 6 taken along line 7—7.

A sectional view of the apparatus shown in FIG. 6 is depicted in FIG. 7. Base 92 is provided with a bore 93 through which lead screw 88 can pass. A spacing 97 is provided between plate 94 and tray support 98 and is preferably about 0.010 to 0.050 inch wide. Spacing 97 is usually left unfilled, however, it can be filled with a material that permits or promotes uniform heating of tray support 98. Tray support 98 contains a barrier 99 that serves as an alignment guide for tray 100. Finally, tray 100 is confined laterally within tray support 98 by frame 102.

IV. Calibration Units

Figure 8A:
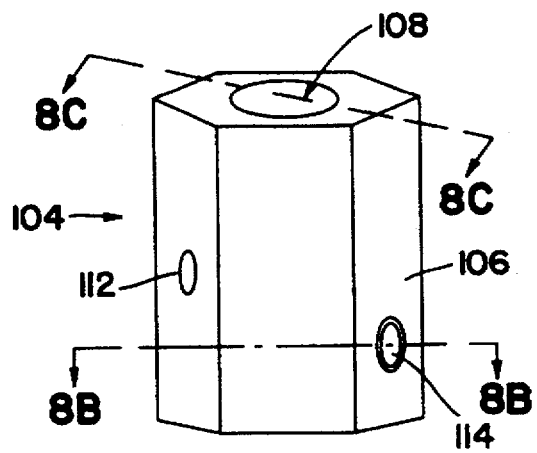
FIG. 8A shows a perspective view of an internal calibration unit constructed according to the present invention.

Depicted in FIG. 8A is an internal calibration unit 104 for use in the present invention. The unit includes an opaque housing 106 which defines an internal cavity 108. A light-emitting diode (LED) 114 is press-fitted into a wall of housing 106 through a hole provided therein, to illuminate cavity 108. Thermistor 112 is inserted into a slot provided in a wall of housing 106 so that the thermistor can sense the temperature of the housing. To ensure good heat transfer to the thermistor, a heat conductive paste can be used to provide intimate thermal contact of thermistor to the housing.

Figure 8B:
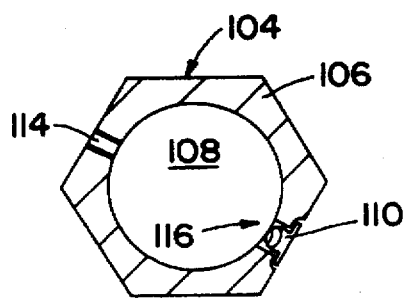
FIGS. 8B and 8C show sectional views of the calibration unit taken along lines 8B—8B and 8C—8C, respectively, in FIG. 8A.

A sectional view of FIG. 8A is presented in FIG. 8B, showing cavity 108 within the unit's housing. As seen, LED 114 and a photodiode 110 are inserted into opposing walls of housing 106 so that light emitted from LED 114 is readily received by photodiode 110.

Figure 8C:
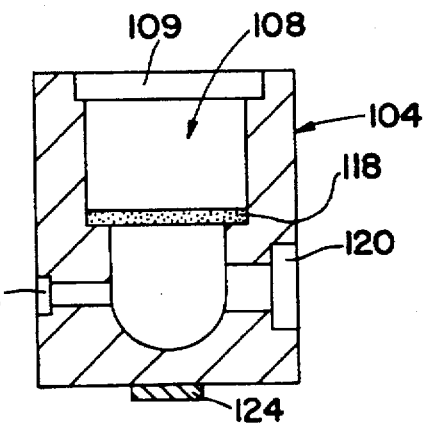

FIG. 8C depicts a second sectional view of internal calibration unit housing. Thus, LED and photodiode receiving ports 122 and 120, respectively, are illustrated. Also shown is an aperture plate 118 which reduces the amount of light emitted from LED 114 into cavity 108, and a diffusion plate 109 to scatter light from the cavity.

Not shown in FIGS. 8A–8C is the control circuitry for regulating the intensity of LED 114 based on light measurements by photodiode 110. Also not shown in the figures is circuitry for controlling a heater 124 based on temperature sensed by thermistor 112. The circuits cooperate to maintain a constant light intensity within cavity 108. Such circuitry is readily apparent to the skilled practitioner and is not discussed further here.

Whenever a photodetection head of a luminometer is desired to be calibrated using calibration unit 104, the photodetection head is moved to an internal-calibration station and aligned with cavity 108. The electrical response of the head, which should be related to the intensity of light emitted by LED 114, is monitored. If the response of the head is outside of a predefined range of acceptable response values, the output of the head can be adjusted to return the response to a value within the desired range. The photoresponse of the head is thereby calibrated for a substantially absolute and constant light intensity.

Figure 9A:
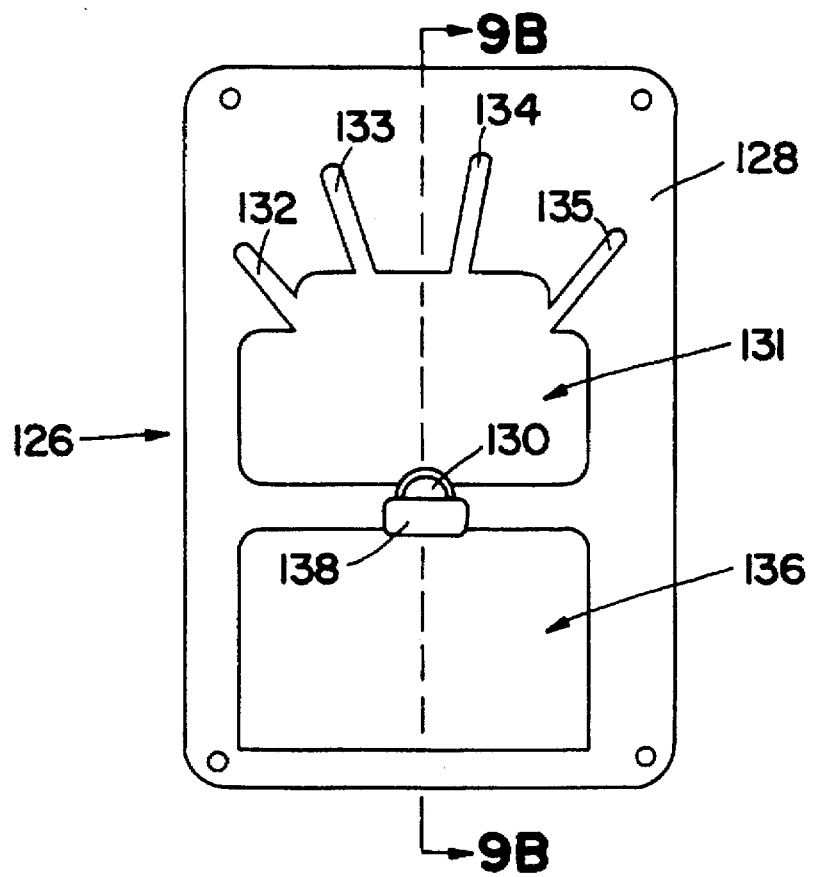
FIG. 9A shows an exploded view of an external calibration unit constructed according to the principles of the present invention.
Figure 9B:
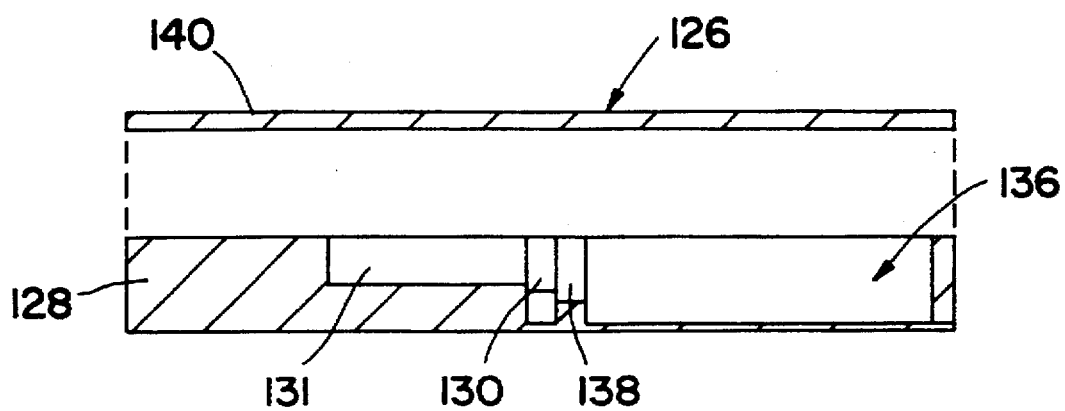
FIG. 9B shows a sectional view of the calibration unit taken along line 9B—9B in FIG. 9A.

In FIGS. 9A and 9B is depicted an external calibration unit constructed according to the principles of the present invention. Calibration unit 126 comprises opaque housing 128 and LED 130 within the housing 128. A cavity 131 defined within the housing 128 is illuminated by LED 130. The calibration unit is constructed to have essentially the same dimensions as a sample tray to permit simple transfer of the unit to a sample tray support whenever a calibration procedure is desired to be performed.

Light channels 132–135 are also provided within housing 128 and are illuminated when LED 130 is activated. Each of channels 132–135 directs light in an arcuate pattern from LED 130 to an aperture from which light can emerge. All of the apertures are substantially equidistant from LED 130 to ensure that a constant radiant flux is incident on the apertures. A cavity 136 is provided in housing 128 behind LED 130 for containing the electrical circuitry for operating LED 130. Power is provided by a battery 138 contained within cavity 136.

The side view shown in FIG. 9B shows a cover plate 140 for housing 128 which prevents light from entering or leaving calibration unit 126. Cover plate 140 is provided with four apertures, e.g., pinholes, (not shown) of varying sizes to permit a range of light intensities to be emitted from cover plate 140 for detection by a photodetection head. Each of the apertures in cover plate 140 is aligned with one of channels 132–135 and the apertures are substantially equidistant from LED 130. The apertures are preferably "drilled" in cover plate 140 with a laser to predetermined diameters. A preferred set of aperture diameters is 100, 316, 1,000, and 3,167 microns, which afford light intensities spanning four orders of magnitude. Additionally, the apertures can be provided at the base of simulated sample wells drilled into the cover plate; however, this is not essential.

External calibration unit 126 can also be provided with a means for heating the unit. In one embodiment, a heating coil can be provided in the base of the unit, which heating coil can be activated outside the unit itself.

Whenever the photoresponse of a detector head is desired to be calibrated with respect to a range of relevant light intensities, e.g., to establish a calibration curve over the range of intensities, the external calibration unit is transferred to the tray support of the luminometer. The head is positioned successively over each of the apertures in the cover plate of the calibration unit and a light measurement is taken. The electrical response generated by the head can be adjusted to coincide with predetermined values, e.g., by adjusting the electrical circuitry or by application of a correction factor(s). The data obtained by these measurements can be subjected to regression analysis to determine a best "fit" for the data or raw data can simply be compared with previously known values and the appropriate adjustments made.

V. Experimental

A luminometer constructed according to the principles of the present invention and a second commercial device were compared for their respective "crosstalk" between sample wells. In these experiments, two identical sample plates were prepared with one plate monitored with a present luminometer (This) and the second plate monitored with the second commercial device (A).

The light generating reactions used a LUMIPHOSE-530™ light generating system. This system includes alkaline phosphatase enzyme and an enzymatically triggerable 1,2,-dioxetane substrate (EP 254,0510) and Schaap, P. et al., Tetra Lett, 28:1159 (1987)). Dephosphorylation of the substrate by alkaline phosphatase (AP) produces an unstable 1,2-dioxetane compound which undergoes a light emitting decomposition. The AP probe was diluted into dioxetane and then pipetted into the sample wells. Half of the wells were covered with MYLAR and the other half were left uncovered. The plates were placed into the luminometers and readings were taken every seven minutes. Crosstalk readings were obtained by reading an empty well adjacent a light-emitting well.

The results are presented in Table 1. The data are in arbitrary units.

TABLE 1

| Luminometer | Signal in Sample well | Signal in Read well | MYLAR | Crosstalk-1 part per |
|---|---|---|---|---|
| A | 251.3 | 0.008 | yes | 31,400 |
| A | 926.9 | 0.041 | yes | 22,600 |
| A | 554.8 | 0.015 | no | 37,000 |
| A | 1114 | 0.008 | no | 139,300 |
| B | 90.6 | 0.09 | yes | 1,000 |
| B | 134.3 | 0.12 | yes | 1,100 |
| B | 88.1 | 0.09 | no | 1,000 |
| B | 129.9 | 0.15 | no | 900 |

The signals obtained in the sample wells monitored by the device of the present invention (A) were consistently higher than those for identical samples monitored by a commercial luminometer (B) device due to greater overall sensitivities for the device of the present invention. The results also show that crosstalk is at least 10-fold lower with this device when MYLAR is employed over the wells and is at least 3-fold lower still in the absence of MYLAR.

Although the present invention has been described in some detail by way of illustration and example for purposes of clarity and understanding, certain obvious modifications can be practiced within the scope of the appended claims. For example, a liquid injection tube(s) can be provided within the luminometer to inject an enzyme substrate solution into a sample well immediately prior to monitoring the light-forming reaction catalyzed by the enzyme.

It is claimed:

1. A method of detecting light emitted from one of a plurality of luminescent samples in opaque wells in a tray comprising:

positioning a photodetection head adjacent to and covering the top surface of a sample well containing one luminescent sample, thereby permitting the head to detect light emitted by the one sample and to substantially isolate the head from light emitted by the remaining samples.

2. The method of claim 1, wherein said sample well is covered by a transparent film against which said photodetection head presses when the head is in its sample-reading position.

\* \* \* \* \*